United States Patent [19]

Hori et al.

[11] Patent Number: 5,017,875
[45] Date of Patent: May 21, 1991

[54] DISPOSABLE SENSOR

[75] Inventors: Tomoshige Hori, Kitamoto; Kensuke Itoh, Kodaira, both of Japan

[73] Assignee: Snow Brand Milk Products Co., Ltd., Hokkaido, Japan

[21] Appl. No.: 409,339

[22] Filed: Sep. 19, 1989

[30] Foreign Application Priority Data

Sep. 26, 1988 [JP] Japan ............................... 63-240522

[51] Int. Cl.⁵ ............................................ G01N 27/02
[52] U.S. Cl. ................................. 324/446; 73/61.1 R; 219/505; 324/444; 324/703; 324/715; 324/724
[58] Field of Search ............... 324/446, 445, 444, 438, 324/439, 703, 696, 694, 713, 715, 722, 724; 73/61.1 R; 204/1 T, 406; 340/622; 219/505, 504

[56] References Cited

U.S. PATENT DOCUMENTS

| 3,414,811 | 12/1968 | Carter | 324/703 |
| 3,579,097 | 5/1971 | Luden | 324/439 |
| 3,935,742 | 2/1976 | Rybak | 324/696 X |
| 4,251,809 | 2/1981 | Cheney | 324/703 X |
| 4,532,797 | 8/1985 | Yang | 324/696 X |
| 4,767,994 | 8/1988 | Hopkins | 324/439 X |
| 4,888,818 | 12/1989 | Schmitt et al. | 324/439 |

Primary Examiner—Kenneth Wieder
Assistant Examiner—Robert W. Mueller
Attorney, Agent, or Firm—Griffin, Branigan & Butler

[57] ABSTRACT

Two lead wires for each, connected to opposite ends of a heat generating element are secured to a holder. These lead wires form four-point-terminals at their other ends and thereby a disposable sensor is provided. A current source and a voltmeter are connected to the terminal and changes in various properties of fluid are determined on the basis of a value of current supplied from the current source and a value of voltage measured by the voltmeter.

12 Claims, 7 Drawing Sheets

DISPOSABLE SENSOR

BACKGROUND OF THE INVENTION

The present invention relates to a disposable sensor used to measure properties, conditions and the other factors of fluid.

In many industrial and scientific fields, it is important to know properties of fluid such as specific gravity and coefficient of viscosity as well as conditions thereof such as temperature, flowing velocity and flow rate, and sensors of various types have already been proposed to measure such factors.

The inventors disclosed, for example, in Japanese Disclosure Gazette No. 1985-152943, a method for measuring changes in properties of liquid substance or semi-solid substance, in which suitable metallic wire is supplied with electric current so that a temperature of the substance as well as a temperature of the metallic wire may be maintained at a predetermined value, simultaneously, a value of such electric current is measured and therefrom a heat transfer coefficient on the surface of the metallic wire is calculated to determine changes in the properties.

The inventors also disclosed, in Japanese Disclosure Gazette No. 1987-185146, a method for measuring conditions of fluid, in which temperatures of one or more sensor elements, a temperature of the fluid and differential temperatures between the respective sensor elements and the fluid are comparatively measured to determine conditions of the fluid. This Disclosure Gazette describes a stainless rod carrying platinum wire wound therearound and then coated with teflon, as a sensor used to perform this method.

It is also known, for example, from, Japanese Disclosure Gazette No. 1986-210959 to form a passage into which a liquid sample is introduced for detection of chemical ingredients thereof within this passage or for the like purposes and to assemble the passage and elements contained therein such as a detecting sensor and a pump into a disposable cartridge.

For properties, conditions and the other factors to be accurately measured, the surface of the sensor brought into contact with fluid to be measured must be free from any contamination.

However, in the well-known art as mentioned above, if said fluid to be measured comprises gelable substance, blood, detrimental substance for human body or the like, it will be difficult for such substance to be completely removed or washed away from the sensor when the sensor is not reused to prevent danger, or even when it is reused, even though the sensor is coated with teflon, and such inadequate washing will prevent the subsequent measurement from being accurately accomplished.

The sensor of said cartridge type contains therein various elements such as the pump and correspondingly, the cartridge itself becomes considerably expensive. With a consequence, the sensor of this type has usually been washed after every measurement and reused several times. Here again, however, washing of the sensor is difficult and troublesome, and the inadequate washing will often adversely affect the subsequent measurement. Thus, such sensor of cartridge type has left the problems of prior art unsolved.

Furthermore, a sensor for measurement of properties of fluid was generally expensive because of its complex mechanism, and the sensor was not suitable for disposable, essentially. The method of the present invention simplifies the structure of the sensor, and therefore, a practical disposable sensor can be constructed.

SUMMARY OF THE INVENTION

A principal object of the present invention is, in view of the drawbacks of the prior art as mentioned above, to provide an inexpensive disposable sensor used to measure properties, conditions and the other factors of fluid.

Such object is achieved, in accordance with the prevent invention, by a disposable sensor utilizing so-called hot wire method to measure changes in various properties of fluid, said disposable sensor comprising two lead wires for each connected to opposite ends of a stretched heat generating element and secured to a holder so as to form a four-point-terminal, a current source and a voltmeter electrically connected to said terminal so that said changes may be determined from a value of current supplied from said current source and a value of voltage indicated by said voltmeter.

A method to measure changes in various properties of fluid utilizing the disposable sensor constructed as mentioned just above will be briefly described. The sensor is placed in a container or the like filled with a fluid sample to be measured so that the heat generating element comes into contact with said fluid. Then, the heat generating element is supplied with electrical current through the lead wires for heat generation, causing heat transfer between the heat generating element and the fluid by conduction and convection while the current source and the voltmeter are electrically connected to the terminal defined by the lead wires secured to the holder to supply the heat generating element with electrical current of a predetermined level via the lead wires and to measure the voltage applied to the heat generating element by the voltmeter, and changes in said heat transfer relating to the changes in various properties of fluid can be measured.

It should be understood that the sensor once brought into contact with the fluid and used for measurement may be disposed and replaced by a fresh sensor.

Such disposable sensor of the present invention has advantageous effects as following:

According to the present invention when for example, changes in properties of fluid is measured, the sensor provided separately of a measuring unit proper is disposable, and thus, it is inexpensive and an accurate measurement can be achieved. Moreover, not only a requirement for troublesome operation of sensor washing after every measurement is eliminated, but also a possibility that an operator might be exposed to toxicity of measured fluid is minimized.

Especially, it is important in practice that the measurement is performed with a sensor always free from contamination and, therefore, neither a measurement error due to such contamination on the sensor surface nor contamination of the fluid due to contamination of the sensor surface occurs.

Furthermore, there is no requirement for recovery of the sensor after every measurement, so the sensor of the present invention can be used for the fluid of special types, for example, as cast iron within the blast furnace.

The structure of the sensor itself simply comprising platinum wire or the like serving as the heat generating element, the lead wires and the holder for said lead wires can be easily manufactured at a cost reasonably low to provide it as a disposable sensor.

By constructing the sensor as a sufficiently small sensor having a correspondingly shorter heat generating element, it will be also possible to measure properties and the other factors of fluid at any location within this fluid.

BRIEF DESCRIPTION OF THE DRAWINGS

The above and other objects of the invention will be seen by reference to the description taken in connection with the accompanying drawings, in which.

DETAILED DESCRIPTION OF THE INVENTION

The disposable sensor of the present invention utilizes the fact that changes in various value of properties of fluid is definitely related one-to-one to changes in heat transfer coefficient.

A coefficient of heat transfer $\alpha$ on the surface of the heat generating element fixed in the fluid is expressed by an equation $$\alpha = Q/S \, (\theta_s - \theta_\infty) \quad (1)$$

where
Q: a calorific power of the heat generating element,
S: a surface area of the heat generating element,
$\theta_s$: a surface temperature of the heat generating element, and
$\theta_\infty$: a temperature of the fluid.

As the inventors disclosed in Japanese Disclosure Gazette No. 1988-132149, the surface temperature $\theta_s$ of the heat generating element is related to an average temperature $\theta_w$ of the heat generating element and the temperature $\theta_\infty$ of the fluid as expressed by a following equation:

$$\theta_s = \theta_\infty + K_1 (\theta_w - \theta_\infty)^{k_2} \quad (2)$$

where $k_1, k_2$: constants specific to individual heat generating elements.

The calorific power Q radiated from the surface of the heat generating element, the surface area S of the heat generating element, the average temperature $\theta_w$ or the heat generating element and the temperature $\theta_\infty$ of the fluid is directly measured according to the common method, and then, a coefficient of heat transfer $\alpha$ can be actually measured.

Figure 1:
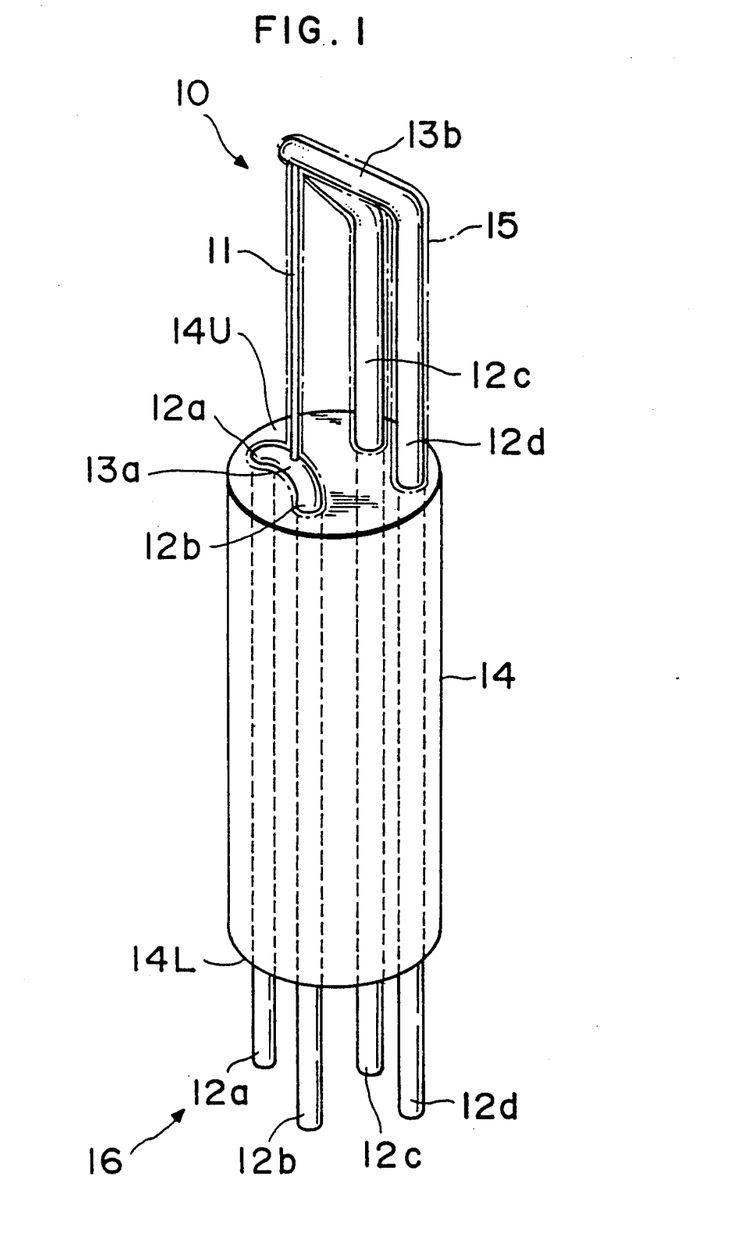
FIG. 1 is a perspective view showing a first embodiment of the disposable sensor constructed in accordance with the present invention.

Now a construction of the disposable sensor according to the present invention will be described in details. FIG. 1 shows a first embodiment of the disposable sensor constructed in accordance with the present invention. The disposable sensor 10 includes a holder 14 made of insulating material through which voltage lead wire sections 12a, 12c and current lead wire sections 12b, 12d extend. The voltage lead wire section 12a and the current lead wire section 12b form together a single lead wire curved in U-shape provided at its upper portion slightly projecting from an upper surface 14U of the holder 14 with a contact 13a.

Similarly, the voltage lead wire section 12c and the current lead wire section 12d form together a single lead wire having its upper portion vertically projecting from the upper surface 14U of the holder 14, and a junction of said section 12c, 12d defines an inverted V-shaped contact 13b which is inclined towards the contact 13a. A heat generating element 11 made of platinum wire is vertically stretched and connected between these contacts 13a and 13b.

As will be apparent, the disposable sensor of the present invention is used to measure voltage values at two ends of the heat generating element by four point-terminal technique without being affected by lead wires.

It should be understood here that not only the heat generating element 11 but also portions of the lead wire sections 12a, 12b, 12c and 12d exposed from the upper surface 14U of the holder 14 are provided with coating 15 preventing electric current from leaking into the fluid, since these portions are to be immersed into the fluid as will be described later.

From a lower surface 14L project the lead wire sections 12a, 12b, 12c and 12d in an appropriate arrangement and form together a terminal 16 to be connected to a connector as will be subsequently described.

Although a combination of the voltage lead wire sections 12a, 12c and the current lead wire sections 12b, 12d is selective, it is also possible, for example, to use the sections 12a, 12c as the current lead wire sections and the sections 12b, 12d as the voltage lead wire sections.

Figure 2:
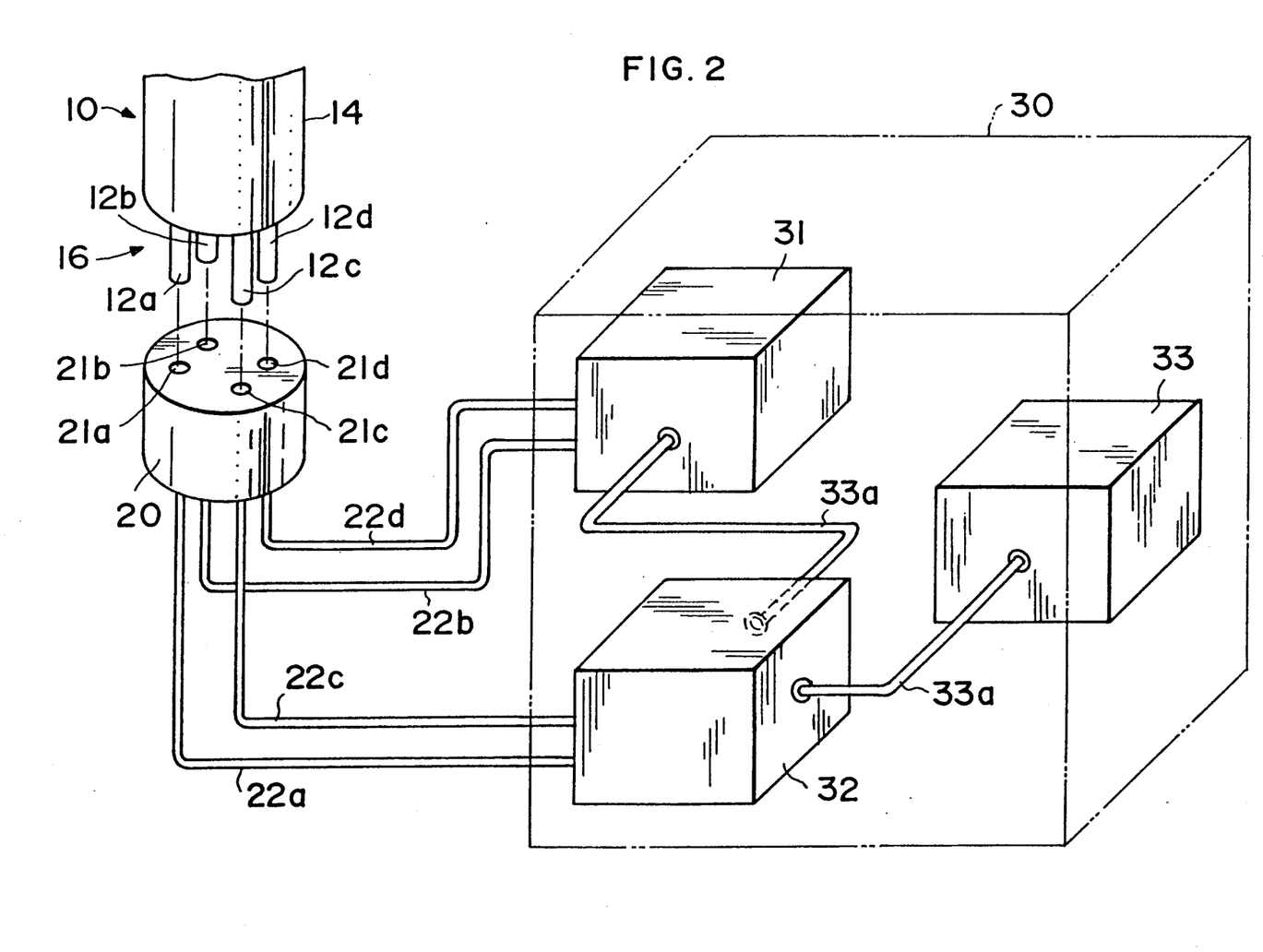
FIG. 2 is a wiring diagram showing a manner in which the disposable sensor of the invention is electrically connected to the measuring unit proper and the internal structure of said measuring unit proper.

FIG. 2 shows a manner in which the terminal 16 of the disposable sensor 10 is electrically connected to a connector 20 which includes sockets 21a, 21b, 21c and 21d with which the lead wire sections 12a, 12b, 12c and 12d of the terminal 16 are mated, respectively. The sockets 21b, 21d connected to the lead wire sections 12b, 12d are electrically connected via lead wires 22b, 22d to a constant current source 31 in a measuring unit proper 30 while the sockets 21a, 21c connected to the voltage lead wire sections 12a, 12c are electrically connected via lead wires 22a, 22c to a voltmeter 32 in the measuring unit proper 30.

Reference numeral 33 designates a controller. This controller 33 and the voltmeter 32, and the constant current source 31 and the voltmeter 32 are respectively connected via communication lines such as GP-IB (general purpose interface bus) cables 33a.

Then, a method for measurement utilizing the disposable sensor 10 of this invention will be discussed.

Figure 3:
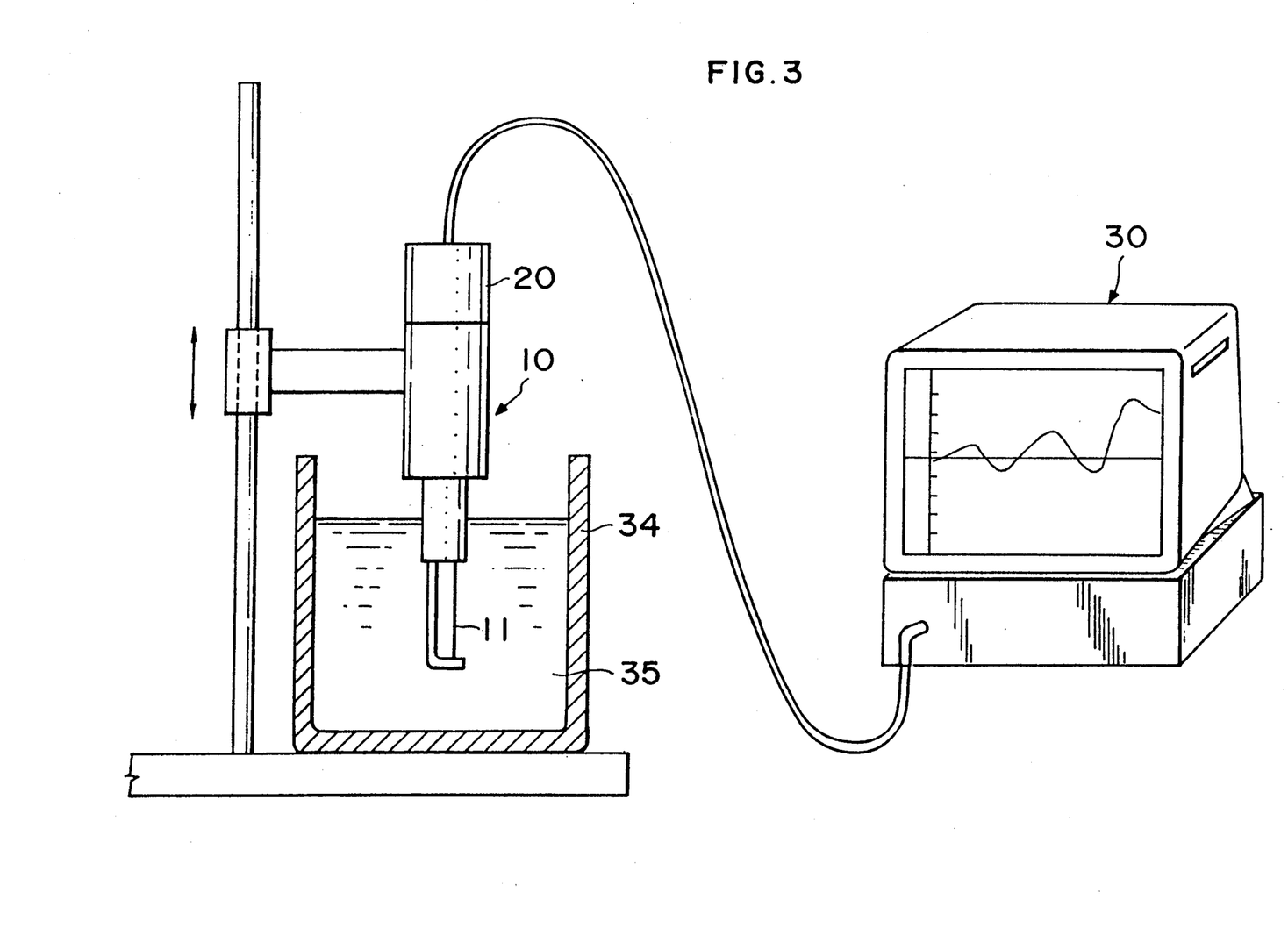
FIG. 3 schematically shows, partially in section, a manner in which the sensor of FIG. 2 is electrically connected to the measuring unit proper.

As seen in FIG. 3, the heat generating element 11 of the sensor 10 connected to the connector 20 is immersed into a quantity of fluid 35 filling a tank 34 with said heat generating element 11 being vertically oriented, and is supplied with electrical current from the constant current source 31 via the current lead wire sections 12b, 12d and the lead wires 22b, 22d so that a calorific power Q is diffused from the heat generating element 11 into the fluid 35 through conduction and convection and, during such diffusion, an applied voltage is measured by the voltmeter 32 via the voltage lead wire sections 12a, 12c and the lead wires 22a, 22c.

Figure 5A:
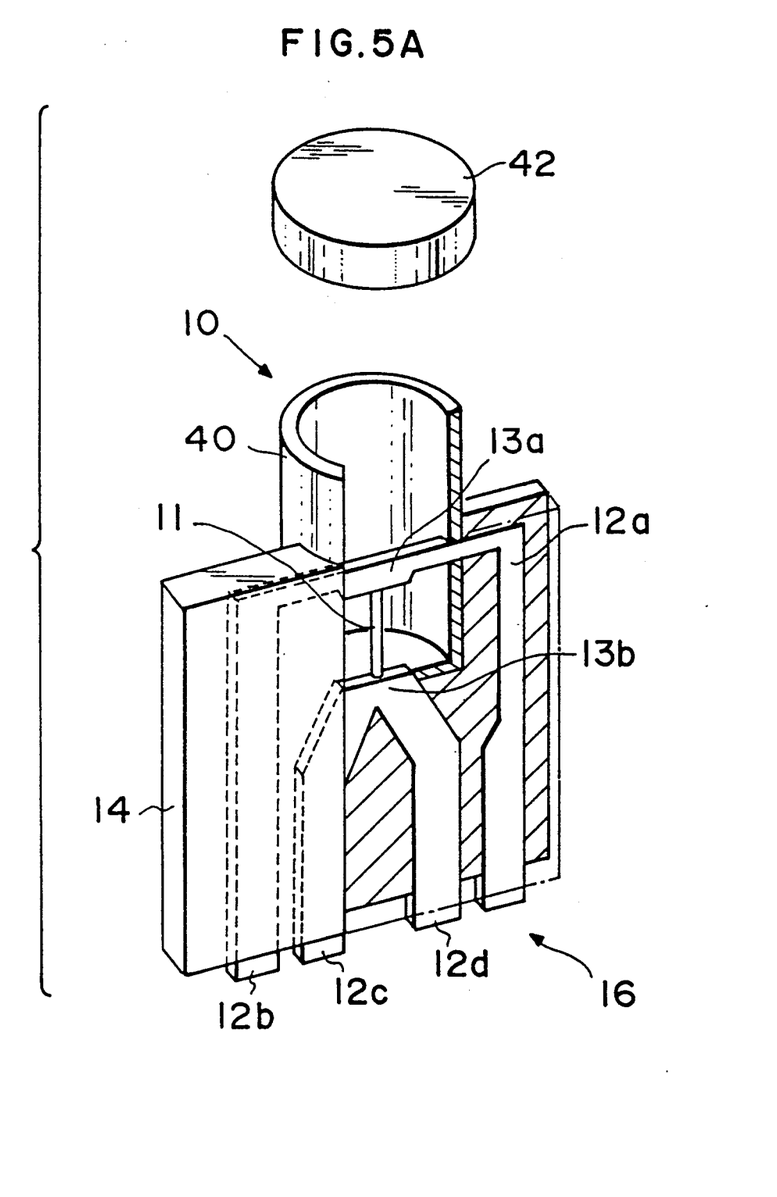
FIG. 5A is a partially broken away perspective view showing a second embodiment of the disposable sensor constructed in accordance with the present invention.
Figure 5B:
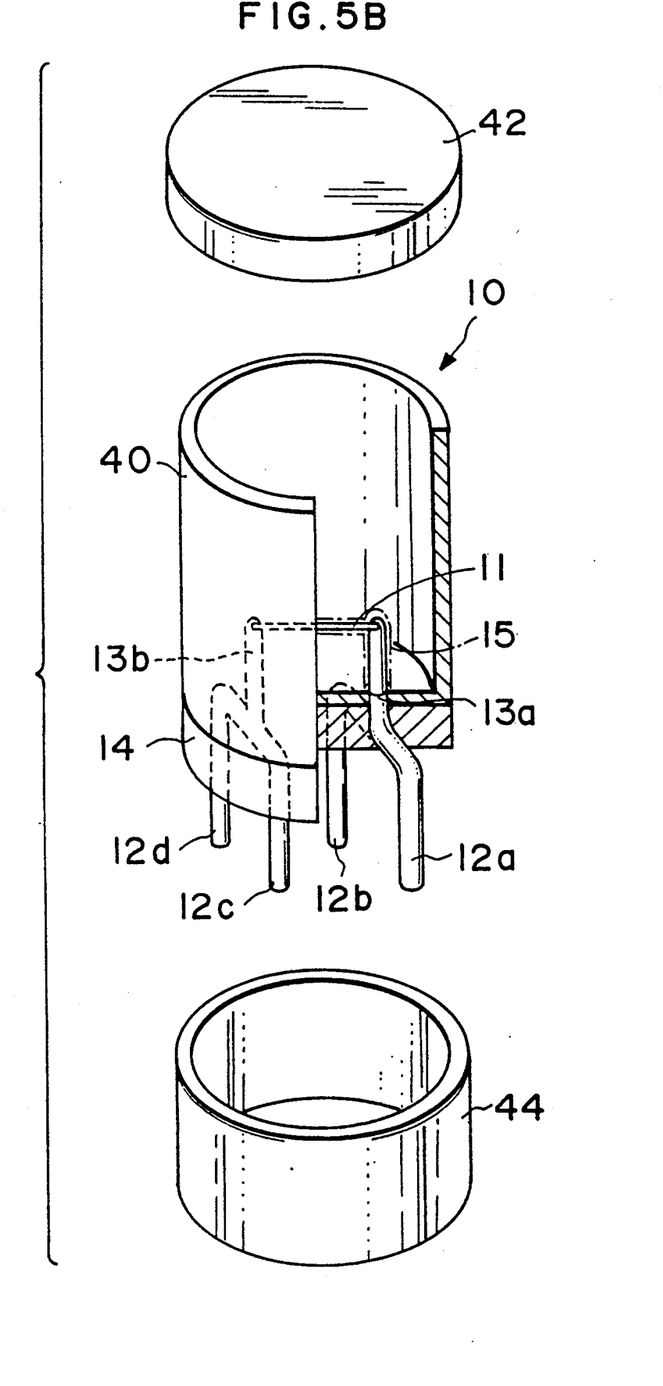
FIG. 5B is a view similar to FIG. 5A but showing a third embodiment of the disposable sensor constructed in accordance with the present invention.

Although it is optimal to maintain the calorific power Q at a constant level by using the controller 33 when changes in fluid temperature is conspicuous, such control can be often effectively achieved by maintaining the current constant in practical use. rp Although it is optimal to stretch the heat generating element 11 vertically between the contacts 13a, 13b, the heat generating element 11 may be also stretched horizontally as in the sensor shown by FIG. 5B in practical use or to any other directions.

By measuring the average temperature $\theta w$ by such sensor, the heat transfer coefficient can be calculated as mentioned above, and thereby change in properties of the fluid such as the coefficient of kinematic viscosity $\gamma$ can be determined.

As the means for measuring $\theta_\infty$, a separate sensor constructed similarly to the sensor 10 of the invention may be placed in the fluid 35 and may be supplied with feeble current in the order of 1 mA to also determine the fluid temperature from the resistance value of this separate sensor, but the thermometric means is not limited to this.

Figure 4:
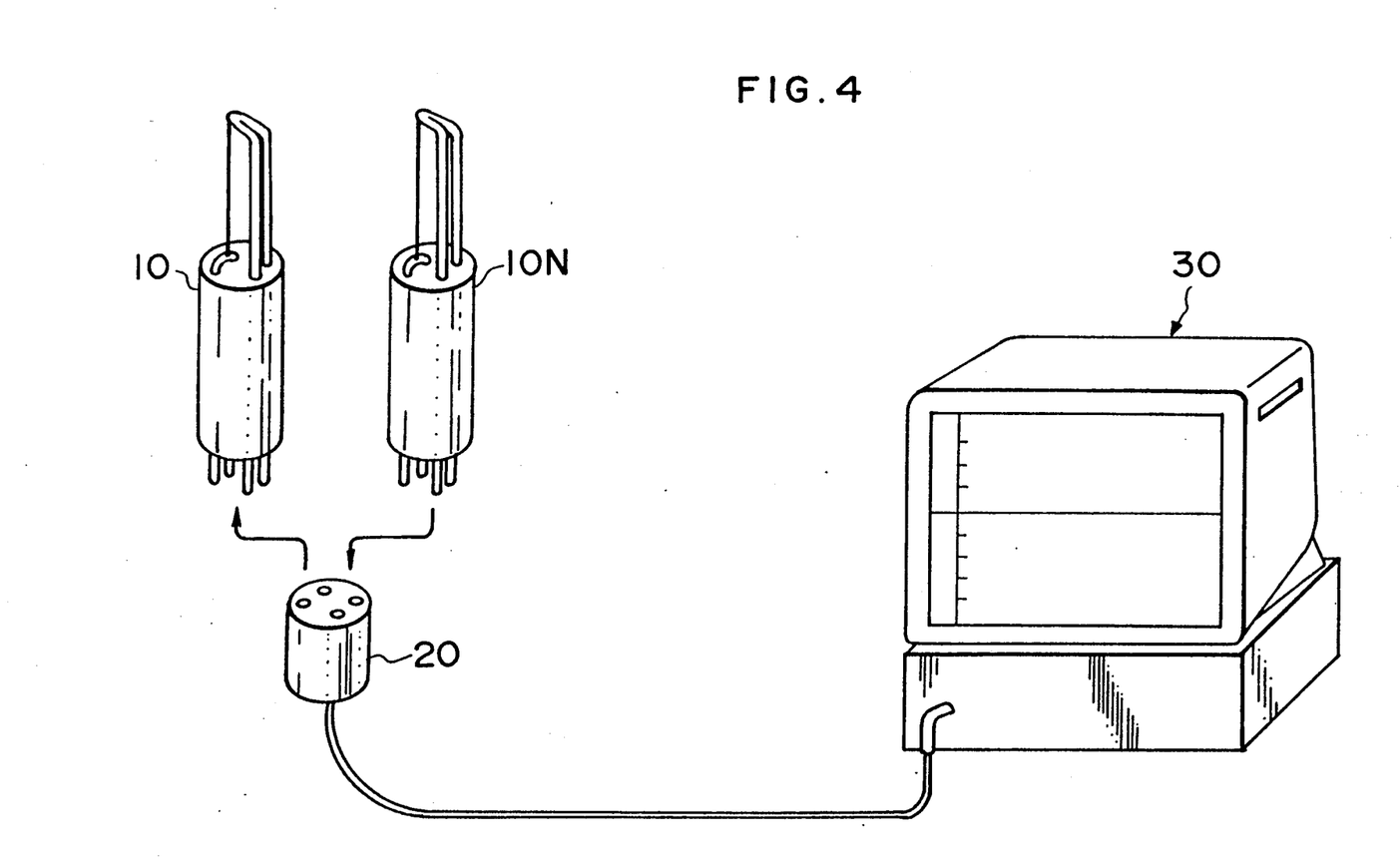
FIG. 4 schematically shows a manner in which the sensor of FIG. 3 is replaced by a fresh sensor.

As seen in FIG. 4 after each measurement of change in value of properties of fluid has been completed, the used sensor 10 is removed from the connector 20 and discarded, then a fresh sensor 10N is mated to the connector 20 for the subsequent measurement or the like.

In this way, both the difficult, troublesome operation of washing the used sensor 10 and the inconvenience that the inadequate washing might prevent the subsequent measurement from being properly performed.

Although the heat generating element has been described by way of example as comprising platinum wire, the other metals or the like may be also used as material for the heat generating element, for example, in addition to platinum, platinum-rhodium, nickel, tungsten, cobalt and molybdenum etc.

Coating material useful for the surface of the heat generating element includes ceramic, various macromolecular substances and resin.

In the place of or onto such coating material, a suitable substance functioning as antibody or antigen may be used or fixed, respectively, to cause antibody or antigen reaction in close proximaty to the surface of the heat generating element immersed in the fluid and thereby to detect characteristics of this fluid under a special condition.

Diemnsioning of the heat generating element is not critical, but a preferable ratio of the outer diameter to the length of the heat generating element is in the order of 1:1000 because such dimensioning makes a heat loss possibly occurring from the ends of the heat generating element negligible and minimizes a measurement error. In practical use, however, the heat generating element presenting the ratio in the order of 1:10, more specifically, the platinum wire having a diameter of 5 to 100 $\mu$m and a length of 1 to 100 mm may be used to provide a sensor which is sufficiently high in measurement accuracy, sensitivity and strength.

FIG. 5A shows a second embodiment of the disposable sensor constructed in accordance with the present invention.

This embodiment is characterized in that the holder 14 is rectangular and the heat generating element is provided within a cylindrical container 40. Correspondingly, the lead wire sections 12a, 12b, 12c, 12d are in the form of rectangular plates. The voltage lead wire section 12a and the current lead wire section 12b are respectively L-shaped, vertically extend from the bottom of the holder 14 at opposite sides thereof, jointed together within the cylindrical container 40 1nd form together a gate-like configuration. The voltage lead wire section 12c and the current lead wire section 12d vertical extend from the bottom of the holder 14 at intermediate positions thereof and jointed together at the bottom of the cylindrical container 40. The contact 13a defined by the junction point of the voltage lead wire section 12a and the current lead wire section 12b is vertical opposed to the contact 13b defined by the junction of the voltage lead wire section 12c and the current lead wire section 12d. The heat generating element 11 is connected vertically between these contacts 13a, 13b.

The lead wire sections 12a, 12b, 12c, 12d define together the rectangular terminal 16 projecting from the bottom of the holder 14.

The construction such that the heat generating element 11 is mounted within the cylindrical container 40 is advantageous in that the fluid can be sampled into this cylindrical container 40 for measurement.

Preferably, the cylindrical container 40 is provided with a lid 42, sheet film or the like to prevent any contaminant often adversely affecting the measurement from entering into the container 40 before every actual measurement is started and to allow the container 40 containing therein the sampled fluid to be transported without spilling the content.

FIG. 5B shows a third embodiment of the disposable sensor 10 constructed in accordance with the present invention, which is similar to the embodiment shown by FIG. 5A except that the heat generating element 11 is horizontally stretched within the cylindrical container 40. Such construction is advantageous in that an effective measurement is possible even when the sampled fluid is of an extremely small amount.

The voltage lead wire section 12a and the current lead wire section 12b are respectively L-shaped, vertically extend from the bottom of the holder 14 at the opposite ends thereof, jointed together within the holder 14 and form together a gate-like configuration. The contact 13a defined by the junction of said sections 12a, 12b vertically extends and is, within the cylindrical container 40, provided with the coating 15. The voltage lead wire section 12c and the current lead wire section 12d are identical to said voltage lead wire section 12a and said current lead wire section 12b. The contact 13b defined by the junction of said section 12c, 12d is opposed to the contact 13a. The heat generating element is horizontally stretched between these contacts 13a, 13b.

Reference numeral 44 designates a cover adapted to be mounted around the location at which the disposable sensor 10 has been mated with the connector 20, not only to assure this mating relationship but also to prevent the fluid from entering into this location and causing a current leakage. More specifically, this cover 44 is provided in consideration of the fact that the terminal 16 comprising the lead wire sections 12a, 12b, 12c, 12d is relatively poor in its strength and the terminal is not provided with insulating coating.

It should be understood that the sensor 10 according to this embodiment also may be provided with the lid 42 or the like to prevent any contaminant from entering into the cylindrical container 40.

Figure 6:
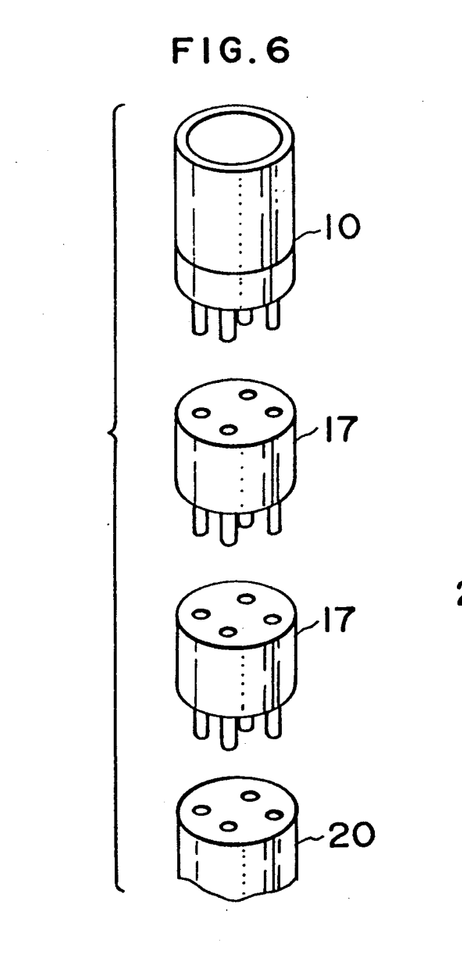
FIG. 6 is a perspective view showing a variant in which the disposable sensor is connected to an electrical connector, both being constructed in accordance with the present invention, utilizing intermediate connectors.

FIG. 6 shows an embodiment in which the sensor 10 is connected by the intermediate connectors 17 to the connector 20 provided on the measuring unit proper 30.

The disposable sensor of the present invention inevitably requires frequent removal of the sensor and this otherwise would progressively reduce a resistance which is necessary for a reliable contact with the connector 20 on the measuring unit proper 30.

To overcome such problem, the present invention provides the intermediate connector 17 on the measuring unit proper 30 so that frequent removal of the sensor directly from the connector 20 on the measuring unit proper 30 may be avoided.

Such intermediate connector 17 may be single, but a plurality of the intermediate connectors 17 may be interposed between the sensor and the connector 20 on the measuring unit proper 30 as shown in FIG. 6 to avoid said undesirably frequent removal of the sensor from the connector 20 on the measuring unit proper 30 more effectively.

Figure 7:
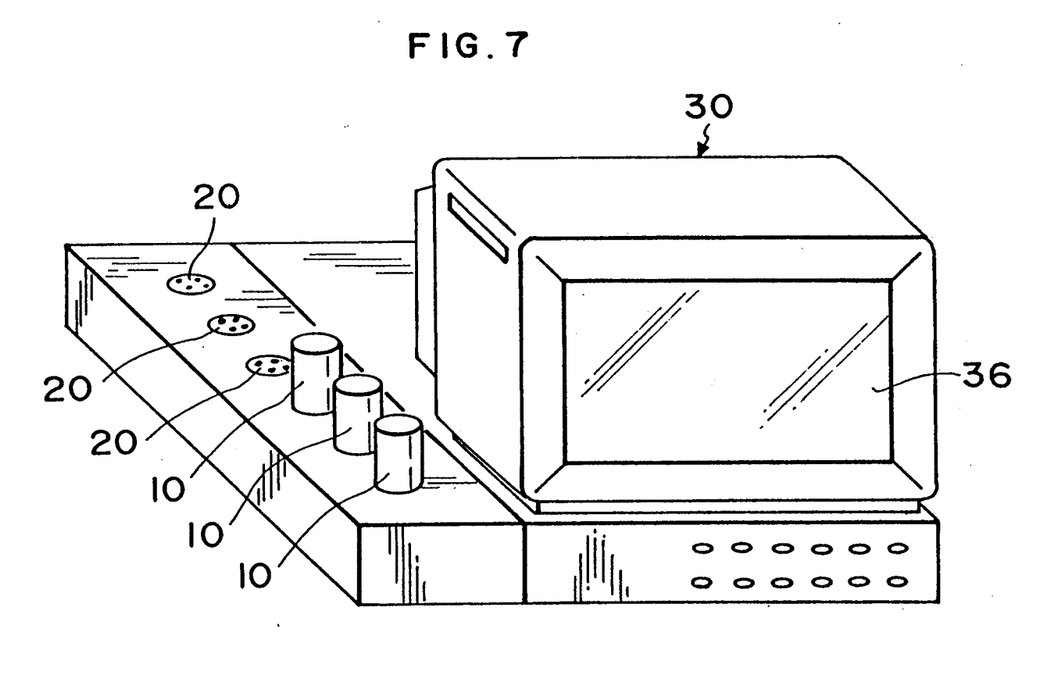
FIG. 7 is a perspective view showing another variant in which a plurality of the disposable sensor of the present invention are electrically connected to the measuring unit proper so that a plurality of fluid samples can be measured at once.

FIG. 7 shows an embodiment in which a plurality of the connector 20 are provided on a side of the measuring unit proper 30 containing the various components such as the constant current source and the volt meter so that a result of measurement can be read on a display 36.

This construction including a plurality of the sensors respectively mated on a series of the connectors 20 permits properties of various fluid samples to be measured at once.

Although the insulating coating for the lead wires and the heat generating element is provided principally in order to prevent a short-circuit due to the current leak, the demand for such coating depends on a situation at which the sensor is to be used and therefore such coating may be provided on any locations so far as such locations require the coating.

Although the embodiments of the invention have been described hereinabove as employing the voltage lead wire and the current lead wire of four-terminal type, it is also possible to mate the sensor with the connector in the two or three-terminal fashion and to distribute the lead wires from the connector in four-terminal fashion.

While the invention has been particularly shown and described with reference to preferred embodiment thereof, it will be understood by those skilled in the art that the foregoing and other change in form and details can be made therein without departing from the spirit and scope of the invention.

What is claimed is:

1. A disposable sensor for measuring changes in properties of fluid, including viscosity and convection heat transfer, said disposable sensor comprising:
   (1) an elongated heat generating element;
   (2) a holder for securing ends of said element;
   (3) lead wires associated with each end of the sensor so as to provide four lead wires connected to a four-point-terminal such that two of the said four lead wires are connected at each end of the heat-generating element;
   (4) a current source connected to two points of the terminal so that changes in the value of the current passing through the heat-generating element are determinable;
   (5) a voltmeter connected to the other two points of the terminal so that changes in the value of the voltage across the heat-generating element are determinable; and
   wherein said changes in the properties of the fluid are determinable from a heat transfer coefficient calculated from a value of the current supplied from said current source and a value of voltage measured by said voltmeter.

2. A disposable sensor as recited in claim 1, wherein the holder is made of insulating material.

3. A disposable sensor as recited in claim 1, wherein the heat generating element and/or the lead wires are provided with a suitable coating.

4. A disposable sensor as recited in claim 3, wherein the coating is made of electrically insulating material.

5. A disposable sensor as recited in claim 3, wherein the coating is made of a substance which is reversibly or irreversibly reactive with the fluid or material containing such substance.

6. A disposable sensor as recited in claim 5, wherein said reversibly or irreversibly reactive substance functions as an antibody or antigen.

7. A disposable sensor as recited in claim 1, wherein the heat generating element is made of platinum, platinum-rhodium, nickel, tungsten, cobalt or molybdenum.

8. A disposable sensor as recited in claim 7, wherein the heat generating element comprises platinum wire having a diameter of 5 to 100 $\mu$m and a length of 1 to 100 mm.

9. A disposable sensor as recited in claim 1, wherein the holder is formed as a container or the holder is provided with a container so that the heat generating element may be mounted within such container 10. A disposable sensor as recited in claim 9, wherein the holder is squarely configured.

11. A disposable sensor as recited in claim 9, wherein the heat generating element is disposed horizontally.

12. A disposable sensor as recited in claim 1, wherein lead wires connected to the said ends of the sensor define a two-point-, or a three-point-terminal connection.

* * * * *